United States Patent [19]

Sheehan et al.

[11] Patent Number: 5,243,709
[45] Date of Patent: Sep. 14, 1993

[54] ACOUSTICALLY SEALING EARMUFF FOR AN INFANT

[75] Inventors: Neil J. Sheehan, Palo Alto; William M. Moore, Foster City; William New, Jr., Woodside, all of Calif.

[73] Assignee: Natus Medical, Inc., Foster City, Calif.

[21] Appl. No.: 754,822

[22] Filed: Sep. 4, 1991

[51] Int. Cl.⁵ ............................................. A42B 1/06
[52] U.S. Cl. ............................................. 2/209; 2/2; 2/423
[58] Field of Search ................ 2/2, 208, 209, 411, 2/412, 413, 414, 423

[56] References Cited

U.S. PATENT DOCUMENTS

| | | | |
|---|---|---|---|
| 2,802,214 | 8/1957 | Hanks | 2/209 |
| 2,883,671 | 4/1959 | Hornickel | 2/209 |
| 3,051,961 | 9/1962 | Clark | 2/2 |
| 3,479,669 | 11/1969 | Allen | 2/209 |
| 3,644,939 | 2/1972 | Beguin | 2/209 |
| 3,823,713 | 7/1974 | Shah | 128/157 |
| 3,841,325 | 10/1974 | Pickard | 128/151 |
| 3,908,200 | 9/1975 | Lundin | 2/209 |
| 3,922,725 | 12/1975 | Csiki | 2/209 |
| 3,938,614 | 2/1976 | Ahs | 181/129 |
| 3,944,018 | 3/1976 | Satory | 181/33 R |
| 4,009,707 | 3/1977 | Ward | 128/27 |
| 4,024,499 | 5/1977 | Bosscher | 340/146.2 |
| 4,036,235 | 7/1977 | Hathaway | 128/292 |
| 4,134,153 | 1/1979 | Voorhees | 2/174 |
| 4,275,744 | 6/1981 | Thornton | 128/731 |
| 4,344,425 | 8/1982 | Strauss | 128/152 |
| 4,408,605 | 10/1983 | Doehrr et al. | 128/402 |
| 4,437,538 | 3/1984 | Ohlsson et al. | 181/129 |
| 4,459,707 | 7/1984 | Stallings | 2/209 |
| 4,551,861 | 11/1985 | Marchello | 2/209 |
| 4,572,323 | 2/1986 | Randall | 2/209 |
| 4,670,911 | 6/1987 | Dunford | 2/209 |
| 4,674,134 | 6/1987 | Lundin | 2/209 |
| 4,682,374 | 7/1987 | Geiser | 2/209 |
| 4,805,239 | 2/1989 | Ciago | 2/24 |
| 4,856,118 | 8/1989 | Sapiejewski | 2/209 |
| 4,905,322 | 3/1990 | Aileo | 2/209 |
| 4,930,520 | 6/1990 | Liverani | 128/746 |
| 4,958,697 | 9/1990 | Moody | 2/423 |
| 4,989,271 | 2/1991 | Sapiejewski | 2/209 |
| 5,020,547 | 6/1991 | Strock | 2/2 |
| 5,023,955 | 6/1991 | Murphy | 2/209 |
| 5,044,014 | 9/1991 | Cornale | 2/423 |

FOREIGN PATENT DOCUMENTS 2010640A 12/1978 United Kingdom .

Primary Examiner—Clifford D. Crowder
Assistant Examiner—Diana L. Biefeld
Attorney, Agent, or Firm—Townsend and Townsend Khourie and Crew

[57] ABSTRACT

A cup member defines a cavity for covering an infant's ear, and an annular member extends from an end portion of the cup member. The cup member and the annular member each comprise a first sound attenuating layer of foam material which attenuates high frequency sound and a second sound attenuating layer of a material which attenuates low frequency sound. The annular member has a surface for placing the earmuff against the infant's head. A hydrogel adhesive is disposed on the surface for bonding the earmuff to the infant's head. The hydrogel layer preferably extends along the plane defined by the surface of the annular member and into the cavity defined by the cup member for bonding the earmuff to a substantially hairless portion of the infant's head located behind the pinna. A portion of the annular member may be creased for forming a bendable tab which helps to conform the earmuff to the curvature of the infant's head behind the ear, and a slit may be formed in the cup member to prevent air pressure build-up in the event of compression of the cup member.

22 Claims, 1 Drawing Sheet

ACOUSTICALLY SEALING EARMUFF FOR AN INFANT

BACKGROUND OF THE INVENTION

This invention relates to sound attenuating devices for ears and, more particularly, to a sound attenuating earmuff for a neonatal infant.

When an infant is in the womb, it is protected from potentially damaging ambient noise by the mother's body. More specifically, the mother's body suppresses sound by approximately 15 dB in the mid to high frequency range. Such sound protection is especially important during the last trimester, since auditory neural pathways begin to form at that time.

Unfortunately, some infants are born prematurely and must be maintained in a neonatal intensive care unit (NICU) of a hospital. Because of the nature of the NICU, much noise throughout the frequency spectrum is generated from the activity of nurses, phones, bells, alarms, etc. Such noises may adversely affect the infant in many ways. For example, the infant's reactions to the stress burns many calories, thus potentially adversely affecting its growth during a critical phase of its life. The noise may keep the infant from getting much needed sleep, and, if antibiotics are administered to the infant, the noise could promote antibiotic attack on sensory mechanisms in the auditory system. Thus, protecting neonatal infants from harmful sounds which arise in the NICU environment is very desirable. On the other hand, since auditory neural pathways are being formed at that time, it is not desirable to attenuate too much sound, because overly isolating the infant from sound may inhibit neural development.

SUMMARY OF THE INVENTION

The present invention is directed to a sound attenuating earmuff for an infant wherein sound is attenuated from approximately 5 dB to approximately 30 dB over the frequency range from approximately 125 Hz to approximately 10,000 Hz. The amount of attenuation is sufficient to protect the child from damaging noise while allowing sufficient sound to pass so as not to interfere with the formation of auditory neural pathways.

In one embodiment of the present invention, a cup member defines a cavity for covering an infant's ear, and an annular member extends from an end portion of the cup member. The cup member and the annular member each comprise a first sound attenuating layer of foam material which attenuates high frequency sound and a second sound attenuating layer of a material which attenuates low frequency sound. The annular member has a surface for placing the earmuff against the infant's head. A hydrogel adhesive is disposed on the surface for removably bonding the earmuff to the infant's head. The hydrogel layer preferably includes a webbed portion which extends along the plane defined by the surface of the annular member and into the cavity defined by the cup member for bonding the earmuff to a substantially hairless portion of the infant's head located behind the pinna. A portion of the annular member may be creased for forming a bendable tab which helps to conform the earmuff to the curvature of the infant's head behind the ear, and a slit may be formed in the cup member to relieve air pressure build-up in the event of compression of the cup member.

DETAILED DESCRIPTION OF THE PREFERRED EMBODIMENTS

Figure 1:
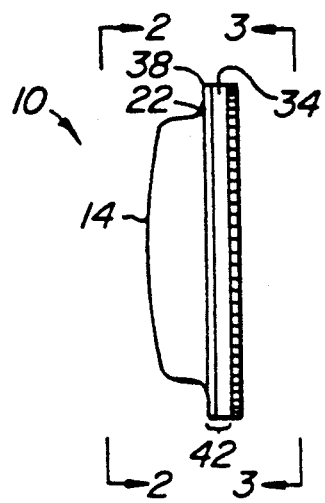
FIG. 1 is a side view of a particular embodiment of a sound attenuating earmuff for an infant according to the present invention.

FIGS. 1-4 are various views of a particular embodiment of a sound attenuating sealing earmuff 10 according to the present invention. Earmuff 10 comprises a cup member 14 defining a generally oval-shaped cavity 18 for covering an infant's ear. Cup member 14 includes an end portion 22 for encircling the infant's ear, and an annular member 26 extends from end portion 22. Annular member 26 has a surface 30 for placing earmuff 10 against the infant's head. An adhesive layer 32, preferably a hydrogel adhesive, is disposed on surface 30 for removably bonding earmuff 10 to the infant's head. A portion of adhesive layer 32 extends into cavity 18 along the plane defined by surface 30 for forming a web 33 at the upper rear portion of cavity 18 for bonding the earmuff to a substantially hairless portion of the infant's head behind the pinna.

Cup member 14 and annular member 26 each comprise a first sound attenuating layer 34 of a material which attenuates (e.g., blocks or absorbs) high frequency sound and a second sound attenuating layer 38 of a material which attenuates (e.g., blocks or absorbs) low frequency sound. In this embodiment, first sound attenuating layer 34 forms the inner surface of the earmuff which faces the infant's ear. First sound attenuating layer 14 is disposed adjacent to second sound attenuating layer 38 and is uniformly bonded thereto. In this embodiment, first sound attenuating layer 34 comprises two to four pounds per cubic foot closed cell polyethylene foam and is approximately one eighth of an inch thick. Second sound attenuating layer 38 preferably comprises low density polyethylene, high density polyethylene, ethylvinyl acetate, a thermoplastic elastomer (TPE), or a blend of two or more of these materials. Second sound attenuating layer is approximately 0.004-0.012 of an inch thick, and preferably approximately 0.008-0.010 of an inch thick. Using dissimilar materials for each layer helps to minimize resonance.

First sound attenuating layer 34 and second sound attenuating layer 38 cooperate to attenuate sound from approximately 5 dB to approximately 30 dB, preferably from approximately 15 dB to approximately 20 dB, over the frequency range of from approximately 125 Hz to approximately 10,000 Hz, preferably from approximately 250 Hz to approximately 8,000 Hz. The distance d (FIG. 4) between the plane defined by surface 30 of annular member 26 and the inner surface of cup member 14 parallel thereto is approximately one quarter inch to minimize the volume of cavity 18. This helps to ensure that cup member 14 does not form a resonant cavity for amplifying ambient sounds which, in turn, could otherwise thwart the sound-attenuating advantages of the present invention. Cup member 14 may be domed or flat, but in this embodiment it is domed to stiffen the earmuff and to further prevent resonant vibration. A domed shape also helps to conform the earmuff to the infant's head.

First sound attenuating layer 34 and second sound attenuating layer 38 terminate in an outer peripheral surface 42 of annular member 26. Outer peripheral surface 42 of annular member 26 preferably is oriented generally perpendicularly to the infant's head so that the generally more rigid second sound attenuating layer 38 does not cause discomfort to the infant should pressure be applied to earmuff 10.

Figure 2:
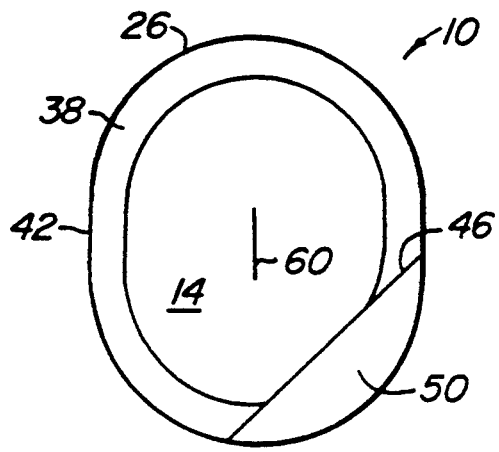
FIG. 2 is an external view of the earmuff taken along line 2—2 of FIG. 1.
Figure 3:
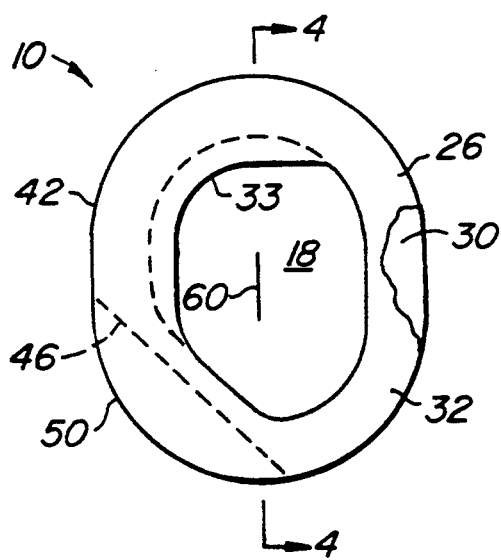
FIG. 3 is an internal view of the earmuff according to the present invention taken along line 3—3 of FIG. 1.
Figure 4:
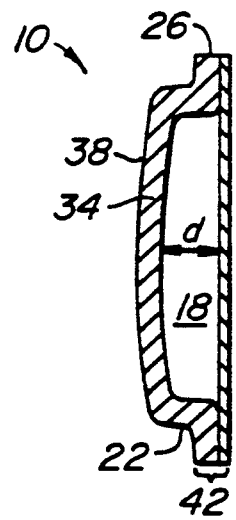
FIG. 4 is a side cross-sectional view of the earmuff according to the present invention taken along line 4—4 of FIG. 3.

As shown more clearly in FIGS. 2 and 3, a portion of annular member 26 has a crease 46 for forming a bendable tab 50 which helps to conform earmuff 10 to the infant's head behind the lower rear portion of the ear. The lower rear portion of cavity 18 is truncated to accommodate tab 50 and to provide for a better fit. An optional horizontal and/or vertical slit 60 may be formed through first sound attenuating layer 34 and second sound attenuating layer 38 in cup member 14 to prevent pressure build up within cavity 18 should cup member 14 be compressed for one reason or another.

While the above is a complete description of a preferred embodiment of the present invention, various modifications may be employed. Consequently, the scope of the invention should not be limited except as described in the claims.

What is claimed is:

1. A sound attenuating earmuff for an infant comprising:
   a cup member defining a cavity for covering an infant's ear, the cup member having an end portion for encircling the infant's ear;
   an annular member extending from the end portion of the cup member, the annular member having a surface for being placed against a portion of the infant's head;
   wherein a portion of the annular member is creased for forming a bendable tab;
   wherein the cup member and the annular member together comprise:
      a first sound attenuating layer of material which attenuates high frequency sound; and
      a second sound attenuating layer of material which attenuates low frequency sound, the second sound attenuating layer being disposed adjacent to the first sound attenuating layer.

2. A sound attenuating earmuff for an infant comprising:
   a cup member defining a cavity for covering an infant's ear, the cup member having an end portion for encircling the infant's ear;
   an annular member extending radially from and generally perpendicularly to the end portion of the cup member for encircling the infant's ear, the annular member having a surface for being placed against a portion of the infant's head;
   wherein the cup member and the annular member each comprise:
      a first sound attenuating layer of material which attenuates high frequency sound; and
      a second sound attenuating layer of material which attenuates low frequency sound, the second sound attenuating layer being disposed adjacent to the first sound attenuating layer;
   an adhesive layer disposed on the surface of the annular member and encircling the infant's ear for bonding the earmuff to the infant's head;
   wherein the adhesive layer extends into the cavity for bonding to a portion of the infant's head located behind the pinna.

3. A sound attenuating earmuff for an infant comprising:
   a cup member defining a cavity for covering an infant's ear, the cup member having an end portion for encircling the infant's ear;
   an annular member extending radially from and generally perpendicularly to the end portion of the cup member for encircling the infant's ear, the annular member having a surface for being placed against a portion of the infant's head;
   wherein the cup member and the annular member each comprise:
      a first sound attenuating layer of material which attenuates high frequency sound; and
      a second sound attenuating layer of material which attenuates low frequency sound, the second sound attenuating layer being disposed adjacent to the first sound attenuating layer;
   wherein the first sound attenuating layer in the cup member is adjacent to the second sound attenuating layer in the cup member along substantially its entire area, and wherein the first sound attenuating layer in the annular member is adjacent to the second sound attenuating layer in the annular member along substantially its entire area.

4. A sound attenuating earmuff for an infant comprising:
   a cup member defining a cavity for covering an infant's ear, the cup member having an end portion for encircling the infant's ear;
   an annular member extending radially from and generally perpendicularly to the end portion of the cup member, the annular member having a surface for being placed against a portion of the infant's head and for encircling the infant's ear;
   wherein the cup member and the annular member each comprise:
      a first sound attenuating layer of foam material which attenuates high frequency sound, the first sound attenuating layer having a thickness of approximately ⅛ inch; and
      a second sound attenuating layer of polyethylene material which attenuates low frequency sound disposed adjacent to the first sound attenuating layer, the second sound attenuating layer having a thickness in the range of from approximately 0.004 inch to approximately 0.012 inch;
   wherein the first sound attenuating layer and the second sound attenuating layer attenuate sound from approximately 5 dB to approximately 30 dB over the frequency range of from approximately 250 Hz to approximately 8,000 Hz; and
   an adhesive disposed on a portion of the first sound attenuating layer that forms the annular member and encircling the infant's ear for bonding the earmuff to the infant's head.

5. The earmuff according to claim 4 wherein the first sound attenuating layer blocks low frequency sound and the second sound attenuating layer blocks high frequency sound.

6. The earmuff according to claim 4 wherein the adhesive comprises a hydrogel layer.

7. The earmuff according to claim 6 wherein the hydrogel layer extends into the cavity for bonding to a portion of the infant's head located behind the pinna.

8. The earmuff according to claim 4 wherein the first sound attenuating layer and the second sound attenuating layer terminate for defining an outer peripheral surface of the annular member.

9. The earmuff according to claim 8 wherein the outer peripheral surface of the annular member is oriented generally perpendicularly to the infant's head.

10. The earmuff according to claim 4 wherein the cup member includes a slit extending through the first sound attenuating member and the second sound attenuating member, the slit being structured for opening and relieving pressure in the cavity upon compression of the earmuff for closing and maintaining sound attentuation when the earmuff is noncompressed.

11. The earmuff according to claim 4 wherein a distance between a plane defined by the surface of the annular member which contacts the infant's ear and an inner surface of the cup member parallel thereto is approximately one quarter inch.

12. The earmuff according to claim 11 wherein the cup member is dome shaped.

13. The earmuff according to claim 4 wherein the first sound attenuating layer in the cup member is adjacent to the second sound attenuating layer in the cup member along substantially its entire area, and wherein the first sound attenuating layer in the annular member is adjacent to the second sound attenuating layer in the annular member along substantially its entire area.

14. A sound attenuating earmuff for an infant comprising:
a cup member defining a cavity for covering an infant's ear, the cup member having an end portion for encircling the infant's ear;
an annular member extending from the end portion of the cup member, the annular member having a surface for being placed against a portion of the infant's head;
wherein a portion of the annular member is creased for forming a bendable tab;
wherein the cup member and the annular member each comprise:
  a first sound attenuating layer of foam material which attenuates high frequency sound, the first sound attenuating layer having a thickness of approximately ⅛ inch; and
  a second sound attenuating layer of polyethylene material which attenuates low frequency sound disposed adjacent to the first sound attenuating layer, the second sound attenuating layer having a thickness in the range of from approximately 0.004 inch to approximately 0.012 inch;
wherein the first sound attenuating layer and the second sound attenuating layer attenuate sound from approximately 5 dB to approximately 30 dB over the frequency range of from approximately 250 Hz to approximately 8,000 Hz; and
an adhesive disposed on a portion of the first sound attenuating layer that forms the annular member for bonding the earmuff to the infant's head.

15. A sound attenuating earmuff for an infant comprising essentially of:
a first sound attenuating layer of foam material which attenuates high frequency sound;
a second sound attenuating layer of material which attentuates low frequency sound;
wherein the first sound attenuating layer and the second sound attenuating layer are disposed adjacent to and contact each other over substantially their entire area;
wherein the first sound attenuating layer and the second sound attenuating layer are formed into:
a cup member defining a cavity for covering an infant's ear, the cup member having an end portion for encircling the infant's ear;
an annular member extending radially from and generally perpendicularly to the end portion of the cup member, the annular member having an annular surface for being placed against a portion of the infant's head encircling the infant's ear; and
an adhesive disposed on the annular surface for encircling the infant's ear and bonding the earmuff to the infant's head.

16. The earmuff according to claim 15 wherein the first sound attenuating layer and the second sound attenuating layer together attenuate sound from approximately 5 dB to approximately 30dB over the frequency range of approximately 250 Hz to approximately 8,000 Hz.

17. The earmuff according to claim 16 wherein the first sound attenuating layer has a thickness of approximately ⅛ inch, and wherein the second sound attenuating layer has a thickness of from approximately 0.004 inch to approximately 0.012 inch.

18. The earmuff according to claim 17 wherein the second sound attenuating layer comprises a polyethylene material.

19. The earmuff according to claim 15 wherein the adhesive comprises a layer of a hydrogel adhesive.

20. The earmuff according to claim 19 wherein the hydrogel adhesive layer extends into the cavity for bonding to a portion of the infant's head located behind the pinna.

21. The earmuff according to claim 15 wherein the first sound attenuating layer is disposed between the infant's head and the second sound attenuating layer when the earmuff is placed against the infant's head.

22. The earmuff according to claim 21 wherein the first sound attenuating layer and the second sound attenuating layer terminate for together defining an outer peripheral surface of the annular member that is oriented generally perpendicularly to the infant's head.

* * * * *